(12) United States Patent
Maruyama (10) Patent No.: US 7,871,219 B2
(45) Date of Patent: Jan. 18, 2011

(54) CONNECTION MECHANISM OF PLATE MEMBER AND SHAFT MEMBER

(75) Inventor: Yoshinori Maruyama, Saitama (JP)

(73) Assignee: Hoya Corporation, Tokyo (JP)

( * ) Notice: Subject to any disclaimer, the term of this patent is extended or adjusted under 35 U.S.C. 154(b) by 27 days.

(21) Appl. No.: 12/137,770

(22) Filed: Jun. 12, 2008

(65) Prior Publication Data

US 2009/0010707 A1    Jan. 8, 2009

(30) Foreign Application Priority Data

Jun. 22, 2007    (JP) .............................. 2007-164778

(51) Int. Cl.
    *F16D 1/08*    (2006.01)
(52) U.S. Cl. ...................... 403/362; 411/315; 411/418
(58) Field of Classification Search ............... 403/1, 403/362; 411/418, 197, 200, 204, 209, 315, 411/217, 219; 285/90, 404; 600/146–149
    See application file for complete search history.

(56) References Cited

U.S. PATENT DOCUMENTS

| | | | | |
|---|---|---|---|---|
| 3,479,484 | A * | 11/1969 | Alleaume | 219/124.34 |
| 3,680,404 | A * | 8/1972 | Firth | 474/33 |
| 4,216,600 | A * | 8/1980 | Brueckner et al. | 42/127 |
| 4,226,133 | A * | 10/1980 | Hanke | 474/42 |
| 4,753,122 | A * | 6/1988 | Nishikawa et al. | 74/424.96 |
| 5,014,685 | A * | 5/1991 | Takahashi | 600/148 |
| 5,163,775 | A * | 11/1992 | Rowan, Jr. | 403/301 |
| 5,393,165 | A * | 2/1995 | Rowan, Jr. | 403/301 |
| 5,501,408 | A * | 3/1996 | Kang et al. | 242/356.5 |
| 5,507,717 | A | 4/1996 | Kura et al. | |
| 5,575,755 | A * | 11/1996 | Krauter et al. | 600/148 |
| 5,662,427 | A * | 9/1997 | Chen | 403/362 |
| 7,128,345 | B2 * | 10/2006 | Bartholoma et al. | 285/137.11 |
| 2005/0137453 | A1 | 6/2005 | Ouchi et al. | |
| 2005/0197532 | A1 | 9/2005 | Sasaki et al. | |
| 2006/0088303 | A1 | 4/2006 | Ito | |

(Continued)

FOREIGN PATENT DOCUMENTS

JP    7-194519    8/1995

(Continued)

OTHER PUBLICATIONS

English language Abstract of JP 7-194519, Aug. 1, 1995.

(Continued)

*Primary Examiner*—Daniel P Stodola
*Assistant Examiner*—Nahid Amiri
(74) *Attorney, Agent, or Firm*—Greenblum & Bernstein, P.L.C.

(57) ABSTRACT

A connection mechanism is provided with a shaft member formed with an outer-screw portion which is formed with an outer screw, a plate member formed with a connection hole in which the shaft member is fitted, a nut member formed with an inner-screw to engage with the outer-screw of the shaft member, the nut member engaged with the shaft member being urged toward the plate member fitted on the shaft member to fixedly secure the plate member onto the shaft member, and a fixing mechanism that fixes the plate member and the nut member with each other to retain a status where the plate member and the nut member are urged oppositely in a rotational direction about a central axis of the shaft member.

6 Claims, 9 Drawing Sheets

U.S. PATENT DOCUMENTS

| | | |
|---|---|---|
| 2007/0010713 A1 | 1/2007 | Negishi |
| 2007/0255104 A1 | 11/2007 | Maruyama |
| 2008/0114377 A1 | 5/2008 | Shibata et al. |

FOREIGN PATENT DOCUMENTS

| | | |
|---|---|---|
| JP | 9-98942 | 4/1997 |
| JP | 10-286220 | 10/1998 |
| JP | 11-47082 | 2/1999 |
| JP | 2003-135384 | 5/2003 |
| JP | 2007-313292 | 12/2007 |

OTHER PUBLICATIONS

English language Abstract of JP 9-98942, Apr. 15, 1997.
English language Abstract of JP 10-286220, Oct. 27, 1998.
English language Abstract of JP 11-47082, Feb. 23, 1999.
English language Abstract of JP 2003-135384, May 13, 2003.
English language Abstract of JP 2007-313292, Dec. 6, 2007.
U.S. Appl. No. 12/137,739 to Maruyama, filed Jun. 12, 2008.
U.S. Appl. No. 12/137,755 to Maruyama, filed Jun. 12, 2008.

* cited by examiner

CONNECTION MECHANISM OF PLATE MEMBER AND SHAFT MEMBER

BACKGROUND OF THE INVENTION

The following descriptions relate to a connection mechanism for connecting a plate member and a shaft member employed, for example, in an endoscope.

Generally, at an operation section of an endoscope, connection mechanisms such as a mechanism for operating a bending portion of an insertion section of the endoscope, a mechanism for changing a rising angle of a treatment tool and the like are provided. Such a mechanism employs a connection mechanism which connects the plate member with the shaft member such that the plate member does not rotate relative to the shaft member.

Typically, in such a connection mechanism, a portion of the shaft member is formed to have an outer-screwed portion. The outer-screwed portion is inserted through an opening formed on the plate member, and with use of a nut having an inner-screw, the plate member is secured to the shaft member. An example of such a configuration is disclosed in Japanese Patent Provisional Publication No. HEI 7-194519.

Figure 10:
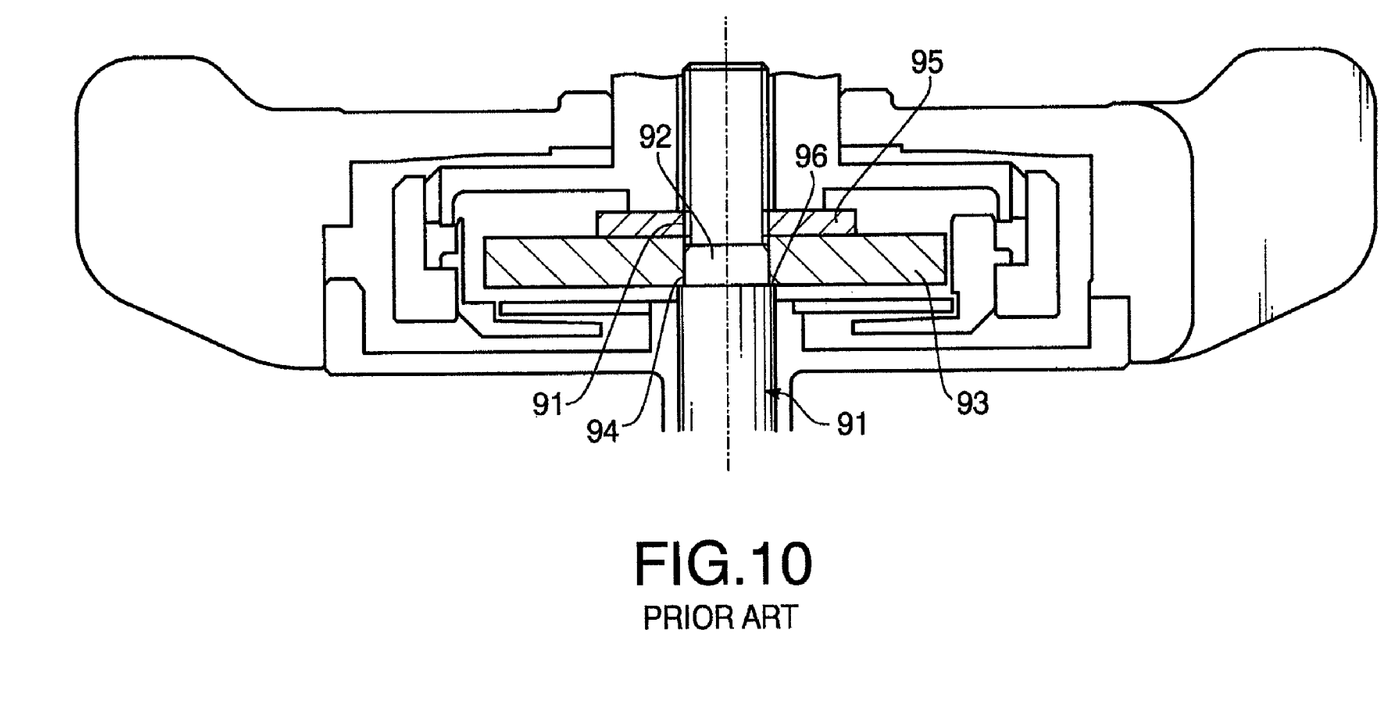
FIG. 10 is a cross-sectional side view of a first example of a conventional connection mechanism.

FIG. 10 shows an example of a conventional connection mechanism. As shown in FIG. 10, a shaft member 90 is formed with a polygonal column section 92 next to an outer-screw section 91. A plate member 93 is formed with a polygonal hole 94 to be fitted on the polygonal column section 92. The plate member 93 is fitted on the polygonal column section 92 and contacts a stepped portion 96 formed at the end of the polygonal column section 92, and urged toward the stepped portion 96 by fastening a nut member 95 provided with an inter-screw which engages with the outer-screw section 91.

Between the polygonal column section 92 and the polygonal hole 94, some play may occur in the rotational direction due to manufacturing errors. Because of such play, fastening of the nut member 95 with respect to the plate member 93 may be loosened in a certain period of time. In such a case, play may occur between the plate member 93 and the shaft member 90.

Figure 11:
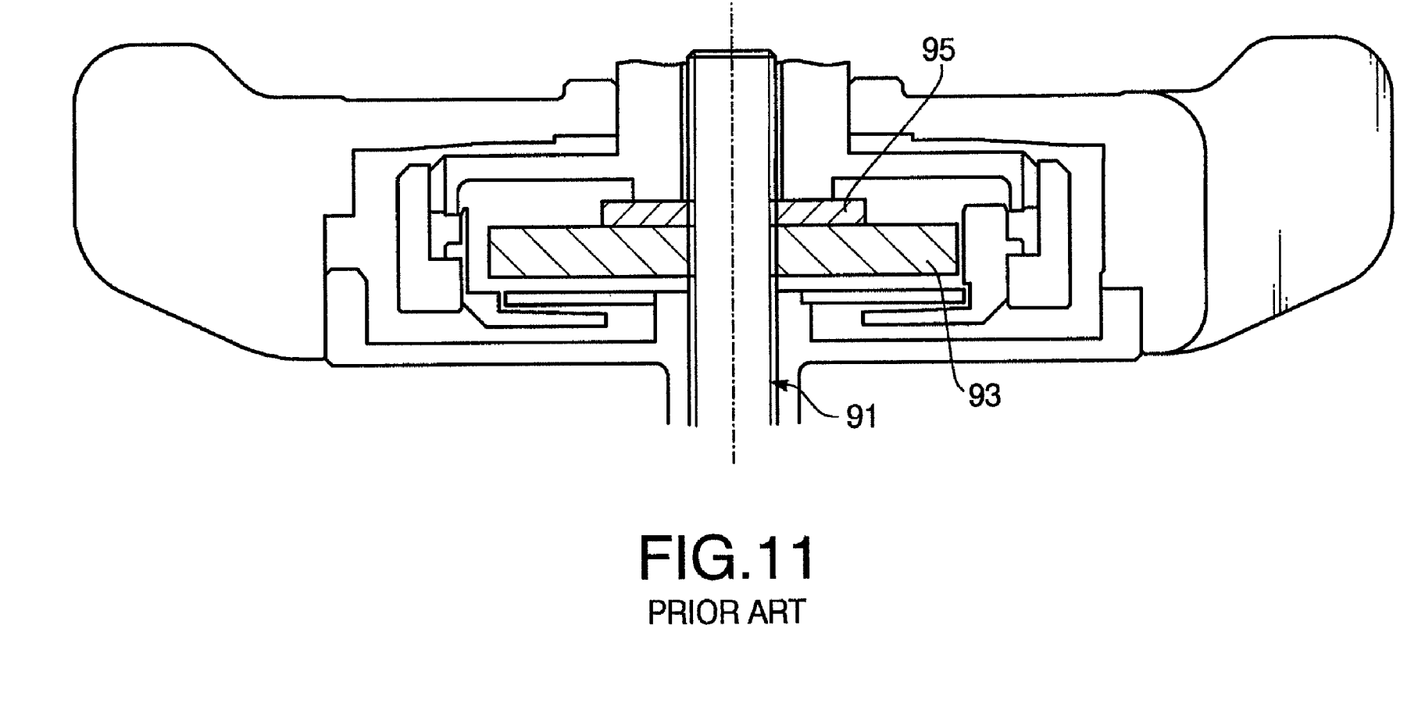
FIG. 11 is a cross-sectional side view of a second example of the conventional connection mechanism.

FIG. 11 shows another example of a conventional connection mechanism. In this example, the shaft member 90 is formed with a cylindrical member formed with an outer-screw, and both the plate member 93 and the nut member 95 engage with the outer-screw of the shaft member such that the plate member 93 and the nut member 95 are urged against each other.

Also in this structure, due to an external force applied to the plate member, the play may occur during usage of the connection mechanism.

SUMMARY OF THE INVENTION

The present invention is advantageous in that an improved connection mechanism, which is configured such that the plate member is secured to the shaft member using the nut member, capable of maintaining secured connected state for a long period.

According to an aspect of the invention, there is provided a connection mechanism, which is provided with a shaft member formed with an outer-screw portion which is formed with an outer screw, a plate member formed with a connection hole in which the shaft member is fitted, a nut member formed with an inner-screw to engage with the outer-screw of the shaft member, the nut member engaged with the shaft member being urged toward the plate member fitted on the shaft member to fixedly secure the plate member onto the shaft member, and a fixing mechanism that fixes the plate member and the nut member with each other to retain a status where the plate member and the nut member are urged oppositely in a rotational direction about a central axis of the shaft member.

With the above structure, the plate member can be secured to the shaft member using the nut member, capable of maintaining a secured connected state for a long period.

DETAILED DESCRIPTION OF THE EMBODIMENTS

Hereinafter, referring to the accompanying drawings, connection mechanisms according to embodiments of the invention will be described.

Figure 2:
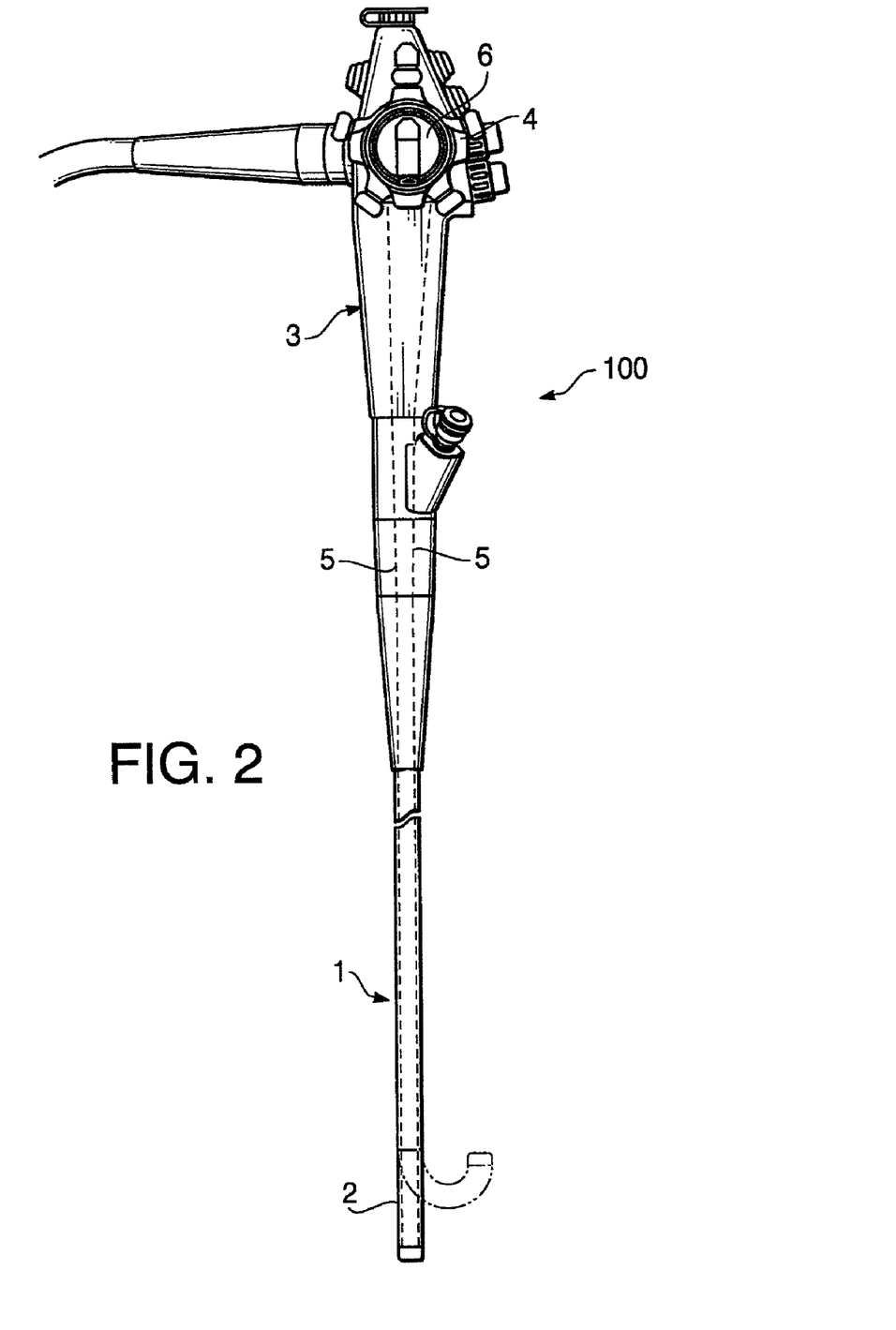
FIG. 2 is a side view of an endoscope employing the connection mechanism shown in FIG. 1.

FIG. 2 shows a side view of an endoscope 100 to which a connection mechanism according to the invention is applicable. The endoscope 100 has a flexible insertion section 1 and a distal end portion thereof is formed to be a bendable section 2. The bendable section 2 is driven by operation of an operation unit 3 connected to the proximal end of the insertion section 1.

Specifically, the operation unit 3 is provided with a bendable section operating knob 4 (hereinafter, simply referred to as a knob), which is rotatable with respect to the operation unit 3. By rotating the knob 4, one of a plurality of operating wires connected to the bendable section 2 is pulled, and the bendable section 2 is bent by an amount (i.e., angle) corresponding to the rotated amount of the knob 4. In FIG. 2, 6 denotes a bent state retaining knob to be used for retaining the bent state of the bendable section 2.

Figure 3:
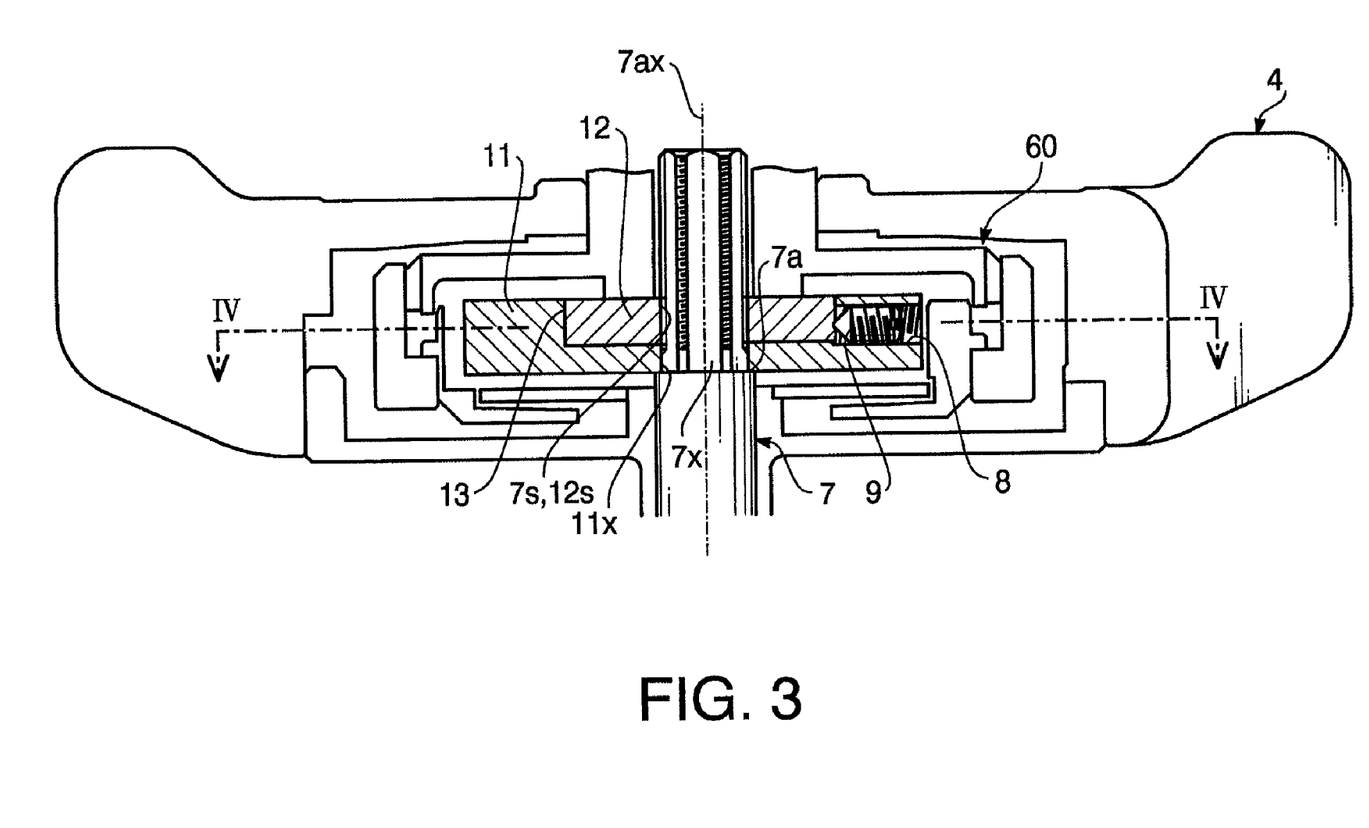
FIG. 3 is a cross-sectional side view of the connection mechanism according to the first embodiment.

FIG. 3 is a cross-sectional side view of the connection mechanism according to the first embodiment. In FIG. 3, 60 denotes a braking mechanism for applying frictional force for preventing the rotational movement of the knob 4 in accordance with the operation of the bent state retaining knob 6. The braking mechanism 60 is of a well-known type, an example of which is disclosed in Japanese Patent Provisional Publication No. 2007-313292. The braking mechanism 60 is secured to a shaft member 7 which is fixedly secured onto the frame of the operation unit 3. A plate member 11 unrotatably engages with the shaft member 7 is fixedly secured thereto by a nut member 12. The plate member 11 serves as a fixed member for braking operation.

It should be noted that the various braking mechanisms have been known, and since the present invention relates to a connection mechanism, which is a part of the braking mechanism and may be applied to other connecting mechanism, the operation of the braking mechanism 60 will not be described for brevity.

The shaft member 7 is provided with a polygonal column portion 7x. According to the first embodiment, a regular hexagonal column is employed. However, any other polygonal column may be used. The shaft member 7 has a cylindrical shape at portions other than the polygonal column portion 7x. At a boundary between the cylindrical portion and the polygonal portion 7x, as shown in FIG. 3, a step 7a is formed.

Figure 1:
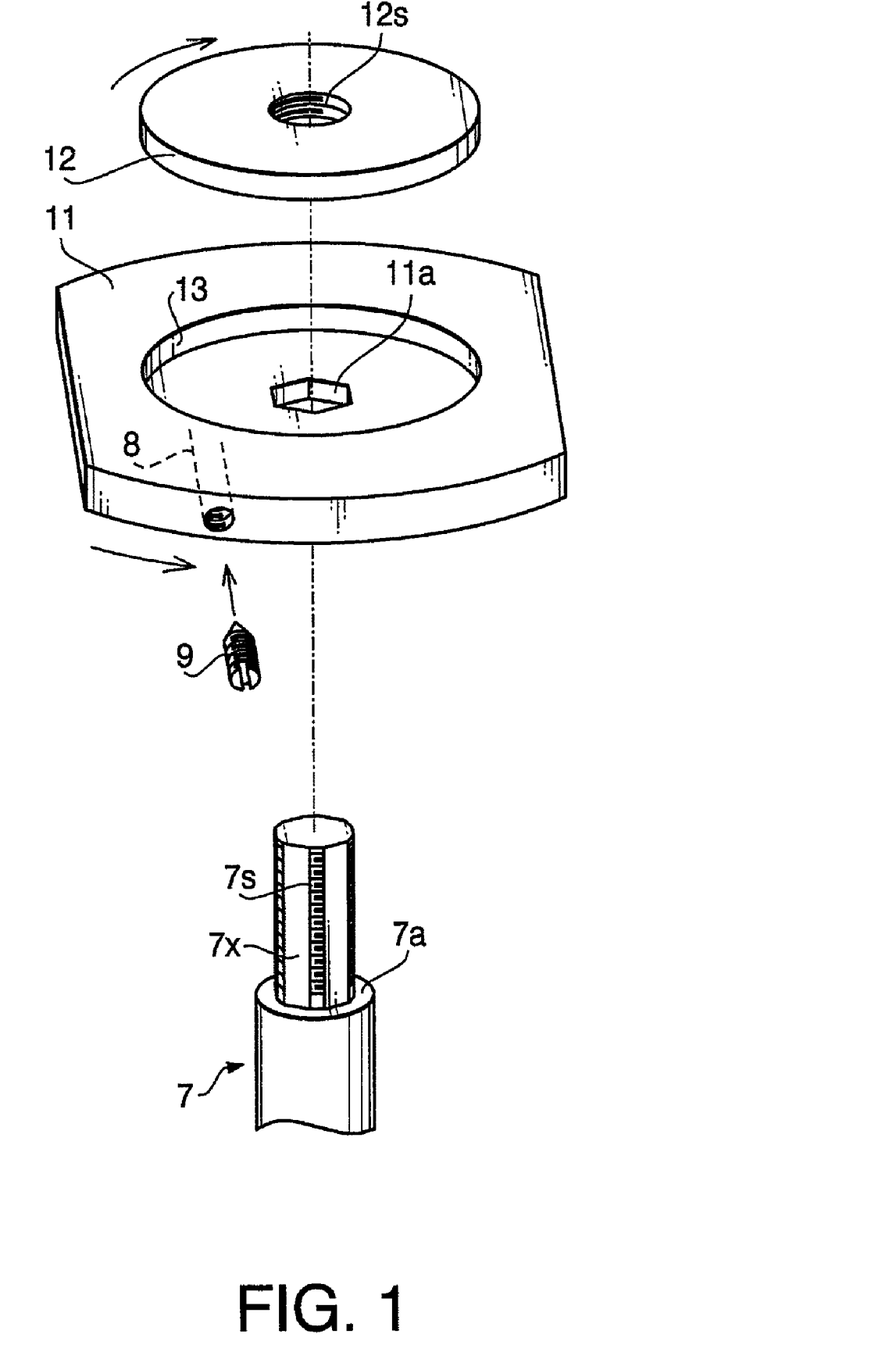
FIG. 1 is an exploded perspective view of a connection mechanism according to a first embodiment.

As shown in FIG. 1, an outer-screw portion 7s is also formed to be a polygonal column shape. That is, the outer-screw is formed on the ridge portions of the polygonal column portion 7x.

The plate member 11 has a connection hole 11a which is formed at the center of the plate member 11. The connection hole 11a has a polygonal shape in which the polygonal column portion 7x of the shaft member 7 is tightly fitted. The nut member 12 has an inner-screw 12s which is formed at the center of the nut member 12. The inner screw 12s engages with the outer-screw 7s of the shaft member 7.

As clearly shown in FIG. 1, the nut member 12 has a disk-like member. On the plate member 11, a circular recess 13 is formed such that the nut member 12 is loosely fitted in the recess 13.

As the polygonal column portion 7x is inserted in the connection hole 11a, the plate member 11 is unrotatably engaged with the shaft member 7. Then, with use of the nut member 12 which screwed on the outer-screw portion 7s, the plate member 11 is urged toward the step portion 7a of the shaft member 7, thereby fixedly secured to the shaft member 7. It should be noted, however, there may exist play between the polygonal column portion 7x and the connection hole 11 in the rotational direction due to manufacturing errors.

Figure 4:
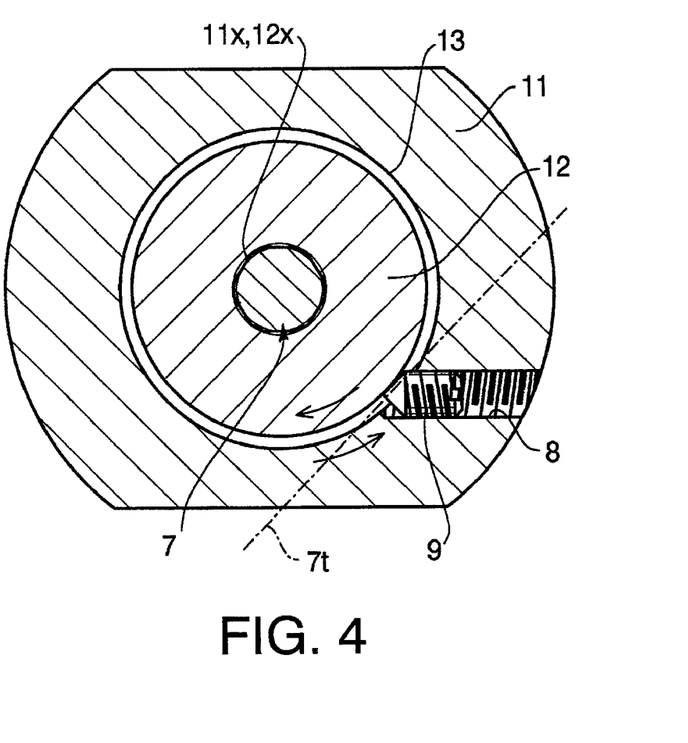
FIG. 4 is a cross-sectional plan view of the connection mechanism taken along line IV-IV in FIG. 3.

As shown in FIG. 1 and FIG. 4, a screw hole 8 is formed on the plate member 11 such that a central axis 8ax of the screw hole 8 extends from an outer circumferential surface of the plate member 11 to the recess 13. As shown in FIG. 4, the direction where the screw hole 8 extends (i.e., the direction of the central axis 8ax of the screw hole 8) is inclined with respect to a tangential line 7t at which the central axis 8ax of the screw hole 8 intersects the circumferential surface of the nut member 12 (i.e., the direction where the screw hole 8 extends is deflected from the radial direction). Further, a screw 9 having a conical tip end is screwed in the screw hole 8 from the outer periphery of the plate member 11 toward the nut member 12.

By fastening the screw 9 tightly, the plate member 11 and the nut member 12 are urged to rotate in opposite directions as indicated by arrows in FIG. 4. With this structure, the fastening force of the nut member 12 for urging the plate member toward the step portion 7a of the shaft is amplified. As a result, the plate member 11 is fixedly secured to the shaft member 7 without any play at all in the rotational direction. It should be noted that the screw hole 8 is formed such that the nut member 12 is urged to rotate in a direction where the urging force applied by the nut member 7 to the plate member 11 increases, as indicated in FIG. 4. If the screw 9 applies force to the nut in the opposite direction, the nut member 12 is loosened.

With the above structure, as the nut member 12 is urged in the direction where the nut member 12 press-contacts the plate member 11, and thus, the plate member 11 is urged toward the step portion 7a, and thus the plate member 11 is fixedly secured to the shaft member 7, and the fixedly secured condition is maintained by the screw 9.

According to the above-described structure, the nut member 12 will not be loosened even after a certain period of time and the play will not occur between the polygonal column portion 7x and the connection hole 11a. Therefore, the tightly connected condition between the plate member 11 and the nut member 12 can be maintained for a relatively long period, stably and without play.

Figure 5:
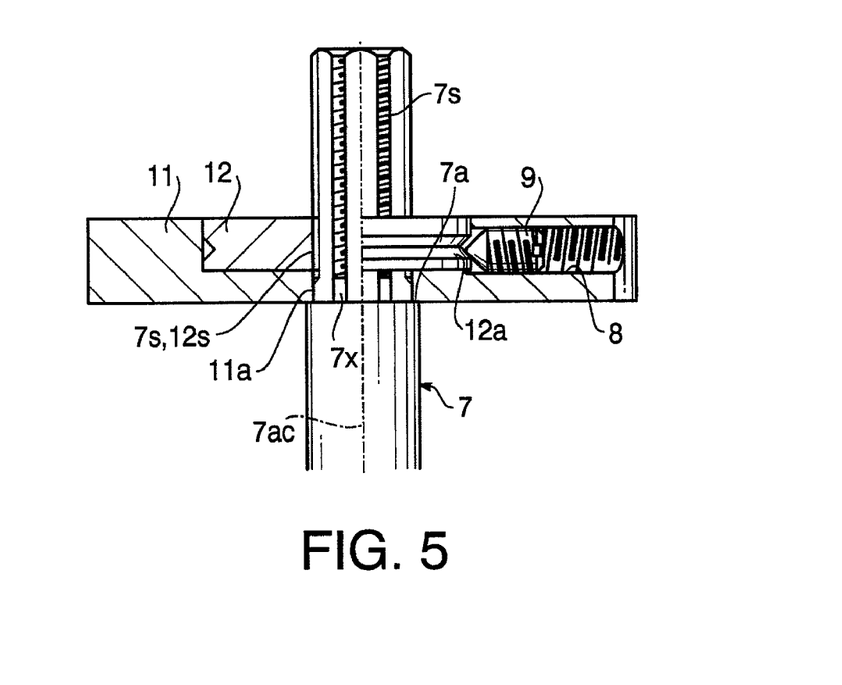
FIG. 5 is a partial cross-sectional side view of the connection mechanism according to a modification of the first embodiment.

FIG. 5 is a cross-sectional side view of a connection mechanism according to a modification of the first embodiment. According to the second embodiment, a groove 12a having a V-shaped cross section may be formed on the circumferential surface of the nut member 12 so that part of the pressing force of the screw 9 is converted to urge the nut member 12 toward the plate member 11.

Figure 6:
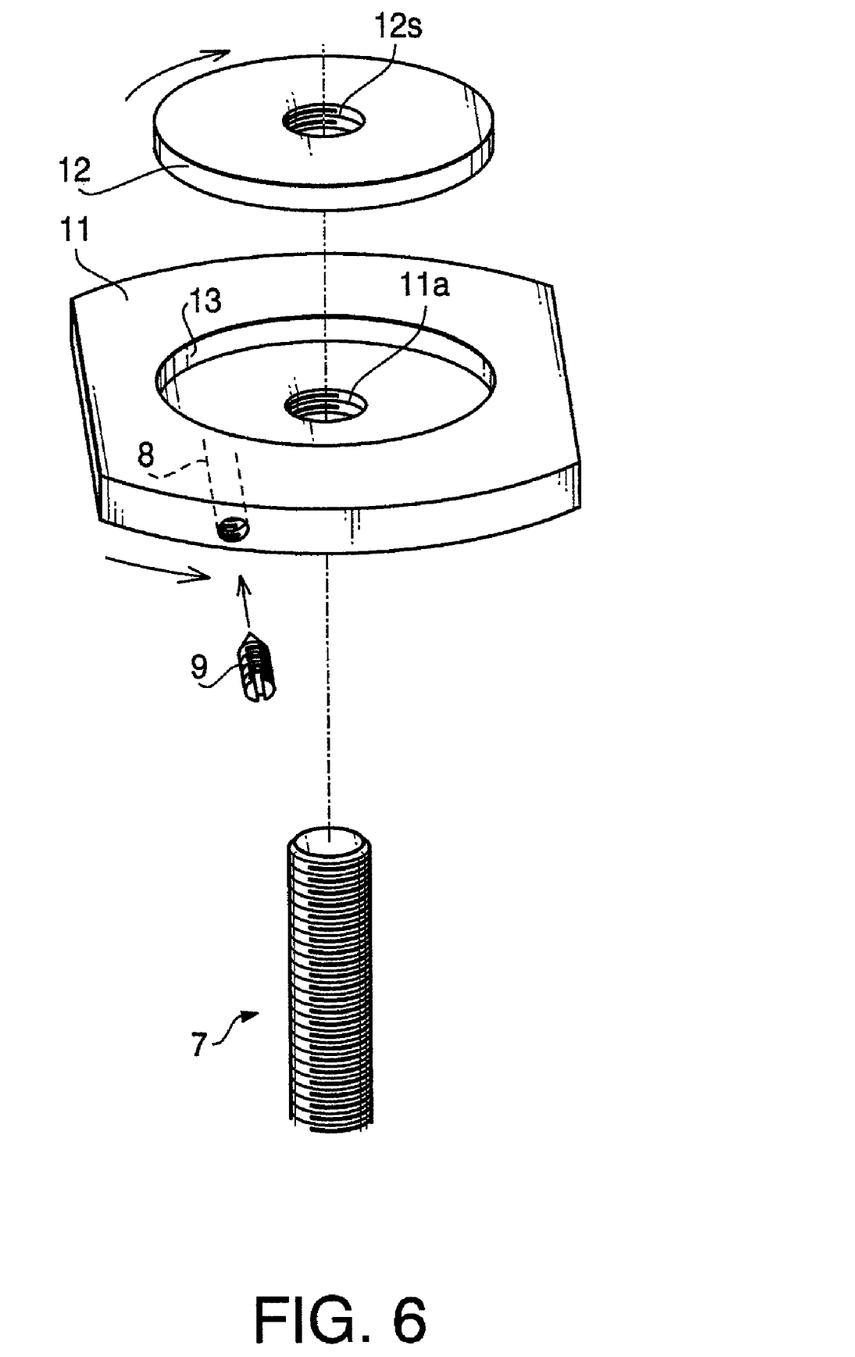
FIG. 6 is an exploded perspective view of a connection mechanism according to a second embodiment.
Figure 7:
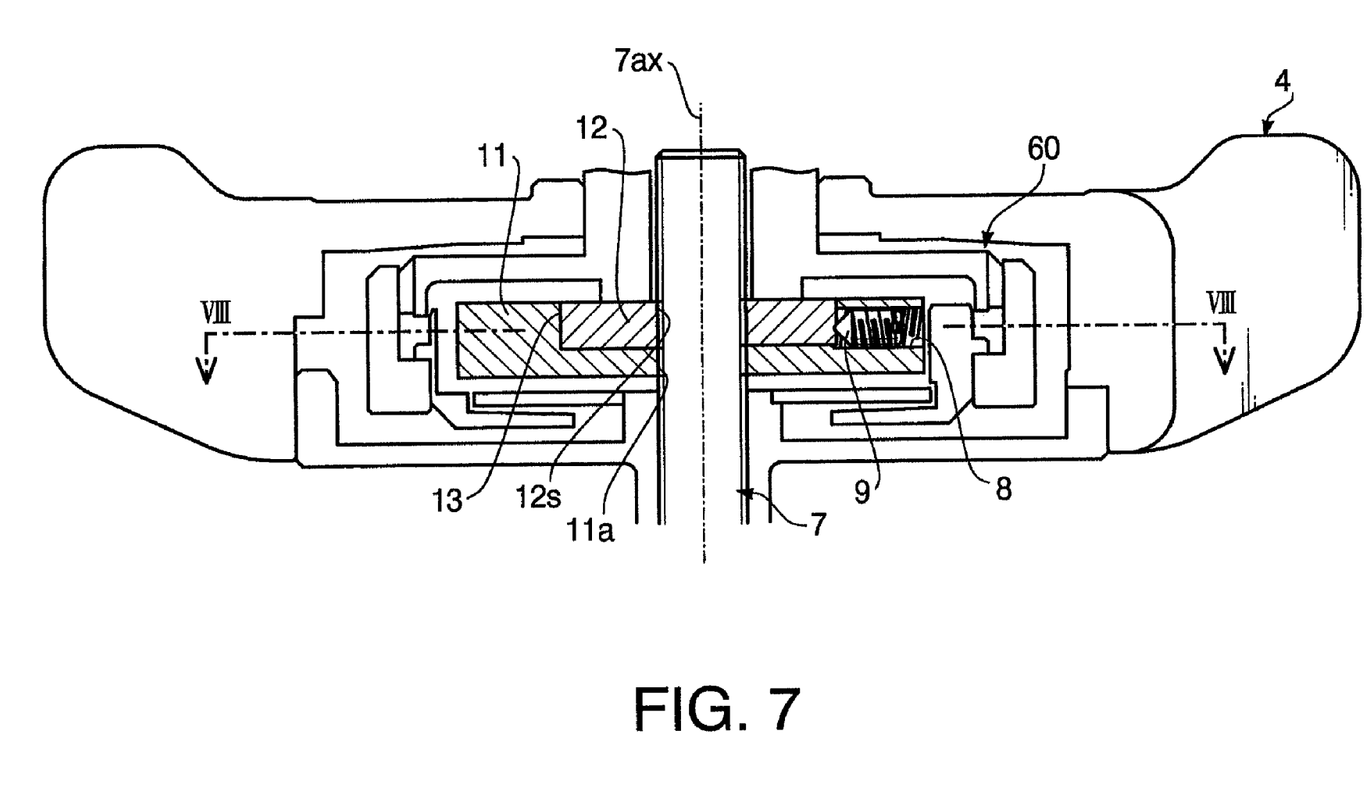
FIG. 7 is a cross-sectional side view of the connection mechanism according to the second embodiment.
Figure 8:
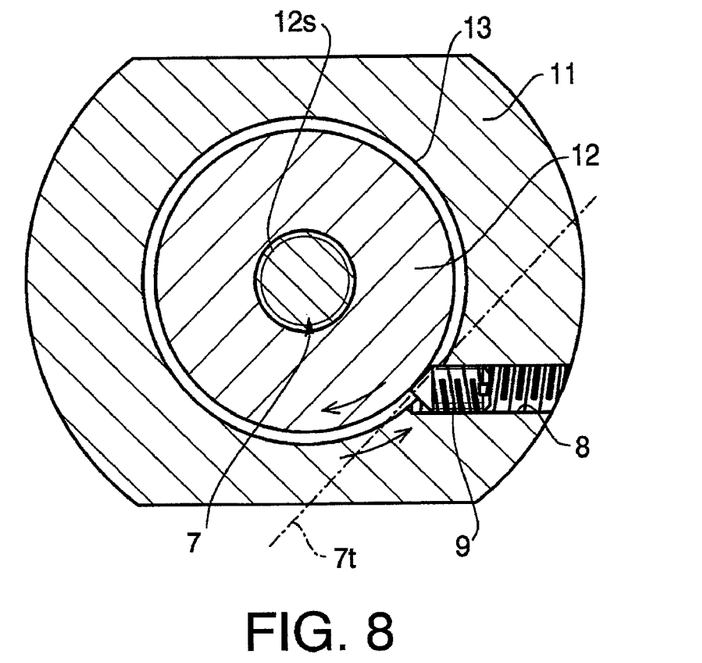
FIG. 8 is a cross-sectional plan view of the connection mechanism taken along line VIII-VIII in FIG. 7.

FIG. 6 is an exploded perspective view, FIG. 7 is a cross-sectional side view of a connection mechanism according to a second embodiment, and FIG. 8 is cross-sectional plan view of the connection mechanism taken along line VIII-VIII of FIG. 7. According to the second embodiment, as shown in FIG. 6, the entire area of the shaft member 7 is formed as a screw (although it is not necessarily be the entire area). In the connection hole 11a, an inner-screw meshes with the outer-screw of the shaft member 7. Thus, both the plate member 11 and the nut member 12 are screwed on the shaft member 7. The other structure is the same as that of the first embodiment.

As a result of the structure according to the second embodiment, the plate member 11 and the nut member 12 can be tightly press-contacted with each other as a double-nut structure, and the tightly press-contacted condition between the plate member 11 and the nut member 12 is amplified by fastening the screw 9. Therefore, the connection state between the plate member 11 and the nut member 12 can be maintained for a relatively long period, without causing the play therebetween.

Figure 9:
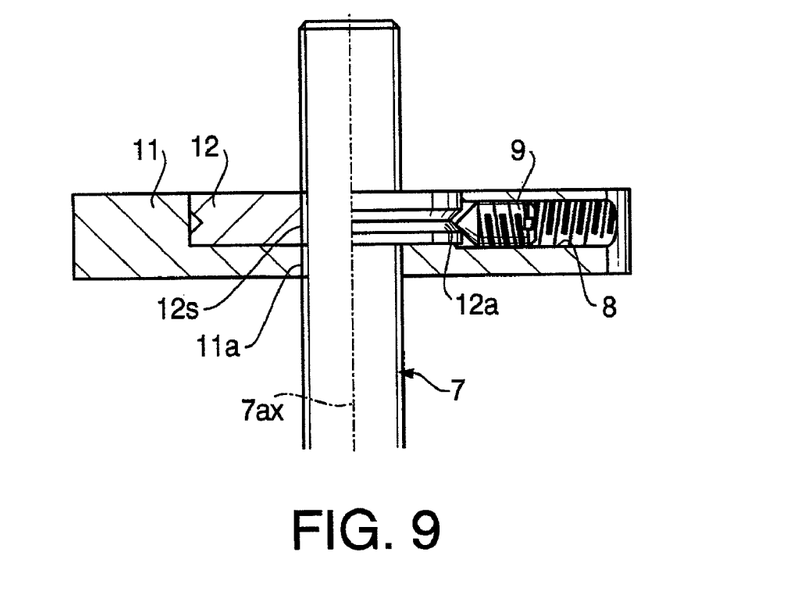
FIG. 9 is a partial cross-sectional side view of the connection mechanism according to a modification of the second embodiment.

As shown in FIG. 9, the second embodiment can be modified as in the modification of the first embodiment. That is, a V-shaped groove 12a may be formed on the outer circumferential surface of the nut member 12 so that part of the pressing force of the screw 9 is converted into the force for urging the nut member 12 toward the plate member 11.

The present disclosure relates to the subject matter contained in Japanese Patent Application No. 2007-164778, filed on Jun. 22, 2007, which is expressly incorporated herein by reference in its entirety.

What is claimed is:

1. A connection mechanism, comprising:
a shaft member formed with an outer-screw portion which is formed with an outer screw;
a plate member formed with a connection hole in which the shaft member is fitted;
a nut member formed with an inner-screw to engage with the outer-screw of the shaft member, the nut member engaged with the shaft member being urged toward the plate member fitted on the shaft member to fixedly secure the plate member onto the shaft member, wherein the plate member is further formed with a recess in which the nut member is fitted; and
a fixing mechanism including:
a screw hole formed in the plate member extending from an outer periphery of the plate member to an outer periphery of the nut member fitted in the recess, the screw hole extending in a direction deflected from a direction toward the central axis of the shaft member;

and a screw inserted in the screw hole, wherein the screw amplifies a fastening force between the plate member and the nut member such that the plate member and the nut member are urged oppositely in a rotational direction about a central axis of the shaft member so that the contacting force between the plate member and the nut member increases.

2. The connection mechanism according to claim 1, wherein the nut member is provided with a groove having a V-shaped wall along an outer-circumferential surface thereof, a tip of the screw contacting the V-shaped wall of the groove thereby enhancing the connecting force between the plate member and the nut member.

3. The connection mechanism according to claim 1, wherein the shaft member is formed with a polygonal column portion next to the outer-screw portion, a stepped portion being formed at the end or the polygonal column portion, wherein the connection hole is formed to be a polygonal hole in which the polygonal column portion of the shaft member fitted, and wherein the nut member screwed onto the outer-screw portion of the shaft member urges the plate member toward the stepped portion.

4. The connection mechanism according to claim 1, wherein the connection hole is formed with an inner-screw to be engaged with the outer-screw portion of the shaft member, and wherein both the plate member and the nut member engage with the outer-screw portion of the shaft member.

5. The connection mechanism according to claim 1, wherein the fixing mechanism engages the plate member and the nut member in a direction generally perpendicular to the shaft member.

6. The connection mechanism according to claim 1, wherein the fixing mechanism extends through the plate member to engage the nut member in a direction generally perpendicular to the shaft member.

* * * * *